(12) United States Patent
Dorsett, Jr.

(10) Patent No.: US 7,908,285 B2
(45) Date of Patent: *Mar. 15, 2011

(54) USER-CONFIGURABLE GENERIC EXPERIMENT CLASS FOR COMBINATORIAL MATERIAL RESEARCH

(75) Inventor: David R. Dorsett, Jr., Slidell, LA (US)

(73) Assignee: Symyx Solutions, Inc., Sunnyvale, CA (US)

( * ) Notice: Subject to any disclaimer, the term of this patent is extended or adjusted under 35 U.S.C. 154(b) by 329 days.

This patent is subject to a terminal disclaimer.

(21) Appl. No.: 11/799,380

(22) Filed: Apr. 30, 2007

(65) Prior Publication Data

US 2007/0203951 A1    Aug. 30, 2007

Related U.S. Application Data

(63) Continuation of application No. 10/351,466, filed on Jan. 24, 2003, now Pat. No. 7,213,034.

(51) Int. Cl.
G06F 7/00 (2006.01)
G06F 17/00 (2006.01)
G06F 9/44 (2006.01)

(52) U.S. Cl. .......................... 707/756; 707/802; 717/108
(58) Field of Classification Search .......................... None
See application file for complete search history.

(56) References Cited

U.S. PATENT DOCUMENTS

| | | | |
|---|---|---|---|
| 4,982,338 A | 1/1991 | Fujita | |
| 5,047,929 A | 9/1991 | Fujita | |
| 5,056,035 A | 10/1991 | Fujita | |
| 5,392,209 A | 2/1995 | Eason et al. | |
| 5,511,186 A | 4/1996 | Carhart et al. | |
| 5,574,656 A | 11/1996 | Agrafiotis et al. | |
| 5,623,592 A | 4/1997 | Carlson et al. | |
| 5,708,806 A | 1/1998 | DeRose et al. | |
| 5,848,415 A | 12/1998 | Guck | |
| 5,959,297 A | 9/1999 | Weinberg et al. | |
| 5,962,013 A | 10/1999 | Wong et al. | |
| 5,980,096 A | 11/1999 | Thalhammer-Reyero | |
| 6,004,617 A | 12/1999 | Schultz et al. | |

(Continued)

FOREIGN PATENT DOCUMENTS

WO    WO 99/33003    7/1999

(Continued)

OTHER PUBLICATIONS

Backofen, R. et al., "Application of constraint programming techniques for structure prediction of lattice proteins with extended alphabets", (Feb. 1999), 17pages.

(Continued)

*Primary Examiner* — Susan Y Chen
(74) *Attorney, Agent, or Firm* — McDermott Will & Emery LLP (57) ABSTRACT

Methods and apparatus, including computer program products, implement techniques for processing experimental data in a laboratory data management system. An input specifies a set of variable definitions that define a set of variables for an experiment type to be represented by a pre-defined experiment class. The variables in the set of variables have types selected from a predefined set of data types. Data from an experiment of the experiment type is received. A first representation of the data is stored in a format defined according to the set of variable types. A second representation of the data, derived from the first representation, is presented in a format defined according to the set of variable definitions.

17 Claims, 10 Drawing Sheets

U.S. PATENT DOCUMENTS

| | | | |
|---|---|---|---|
| 6,030,917 | A | 2/2000 | Weinberg et al. |
| 6,034,775 | A | 3/2000 | McFarland et al. |
| 6,044,366 | A | 3/2000 | Graffe et al. |
| 6,410,331 | B1 | 6/2002 | Schultz et al. |
| 6,415,276 | B1 * | 7/2002 | Heger et al. ............ 706/52 |
| 6,489,168 | B1 | 12/2002 | Wang et al. |
| 6,507,945 | B1 | 1/2003 | Rust et al. |
| 6,618,852 | B1 | 9/2003 | van Eikeren et al. |
| 6,658,429 | B2 | 12/2003 | Dorsett, Jr. |
| 6,754,884 | B1 | 1/2004 | Lucas et al. |
| 6,738,529 | B1 | 5/2004 | Crevier et al. |
| 6,745,368 | B1 | 6/2004 | Boucher et al. |
| 6,947,953 | B2 | 9/2005 | Herzenberg et al. |
| 6,968,536 | B2 | 11/2005 | Jazdzewski |
| 6,983,227 | B1 | 1/2006 | Thalhammer-Reyero |
| 7,188,055 | B2 | 3/2007 | Agrafiotis et al. |
| 7,199,809 | B1 | 4/2007 | Lacy et al. |
| 7,213,034 | B2 | 5/2007 | Dorsett, Jr. |
| 7,308,363 | B2 | 12/2007 | Eker et al. |
| 7,478,337 | B2 | 1/2009 | Kodosky et al. |
| 2001/0047398 | A1 | 11/2001 | Rubenstein |
| 2002/0049548 | A1 | 4/2002 | Bunin |
| 2004/0044990 | A1 | 3/2004 | Schloegel et al. |
| 2004/0221260 | A1 | 11/2004 | Martin et al. |
| 2005/0130229 | A1 | 6/2005 | Dorsett, Jr. |
| 2005/0267721 | A1 | 12/2005 | Thalhammer-Reyero |
| 2005/0273305 | A1 | 12/2005 | Thalhammer-Reyero |
| 2006/0064674 | A1 | 3/2006 | Olson, Jr. et al. |
| 2006/0168515 | A1 | 7/2006 | Dorsett, Jr. |
| 2006/0277201 | A1 | 12/2006 | Dorsett, Jr. |
| 2007/0050092 | A1 | 3/2007 | Kenyon et al. |
| 2007/0143240 | A1 | 6/2007 | Goldwasser et al. |
| 2007/0185657 | A1 | 8/2007 | Lacy et al. |
| 2007/0214101 | A1 | 9/2007 | Wang et al. |
| 2008/0015837 | A1 | 1/2008 | Smith et al. |

FOREIGN PATENT DOCUMENTS

| | | |
|---|---|---|
| WO | WO 00/23921 | 4/2000 |
| WO | WO 01/79949 | 10/2001 |
| WO | WO 02/054188 | 7/2002 |
| WO | WO 03/005249 | 1/2003 |

OTHER PUBLICATIONS

Raynor, W., The International Dictionary of Artificial Intelligence, (1999), p. 63 and cover only.

Shaheen, M. et al., "Remote Laboratory Experimentation", *Proceedings of the American Control Conference*, Philadelphia, Pennsylvania, (Jun. 1998), pp. 1326-1329.

Thayer, A. "Combinatorial Chemistry Becoming Core Technology at Drug Discovery Companies", *Chem Eng. News*, (Feb. 12, 1996), pp. 57-64.

Umetri Ab, MODDE 4-0 Users Guide, Copyright 1992-1997, pp. 1-1 to 14-2 (229 pages), "Graphical Software for Design of Experiments".

Zou, J. et al., "Statistical Theory of Combinatorial Libraries of Folding Proteins: Energetic Discrimination of a Target Structure", *J Mol Biol*, vol. 296 (2000), pp. 281-294.

Arita et al., "Improvement of a Row Displacement Algorithm For Sparse Table Compression", IEEE 1996 1730-1735.

Briceno et al., Science 270, (1995) pp. 273-275.

Bayard et al. "Connecting Scientific Programs and Data Using Object Databases", IEEE Data Engineering Bulletin, vol. 16, 1993, (6 pages).

Berard et al., "Scientific Data Management in the Environmental Molecular Sciences Laboratory", Proc. 14th IEEE Symposium on Mass Storage Systems, 1995 (17 pages).

Chen et al., "An Overview of the Object Protocol Model (OPM) and the OPM Data Management Tools", Information Systems, vol. 20, 1995, pp. 393-418.

Ioannidis et al., "Conceptual Schemas: Multi-Faceted Tools for Desktop Scientific Experiment Management", Int. J. Cooperative Information Systems, vol. 1, 1992 (24 pages).

Ioannidis et al., "Desktop Experiment Management", IEEE Data Eng. Bull., vol. 16, 1993, pp. 19-23.

Ioannidis et al., "FROG and TURTLE: Visual Bridges Between Files and Object-Oriented Data", Proc. Of the 8th International Conference on Scientific and Statistical Database Management, Stockholm, Sweden, 1996, pp. 76-85.

Ioannidis et al., "ZOO: A Desktop Experiment Management Environment", Proceedings of the 22nd VLDB Conference Mumbai(Bombay), India, 1996 (12 pages).

Keller et al., "Metadata: The Foundation of Effective Experiment Management", Proc. of the 1st IEEE Metadata Conference, Silver Springs, Maryland, USA, 1996 (12 pages).

Kling "First Steps Toward a Common Language for Analytical Data", Analytical Chemistry News & Features, Sep. 1, 1999, pp. 621A-623A.

Maier et al., "Bambi Meets Godzilla: Object Databases for Scientific Computing", Proc. of the 7th International Working conference on Scientific and Statistical Database Management, IEEE Computer Society: Washington D.C., USA, 1994, pp. 176-184.

Medeiros et al., "WASA: A Workflow-Based Architecture to Support Scientific Database Applications", Proc. 6th International Conference on Database and Expert Systems Applications, 1995 (20 pages).

Pirklbauer et al., "Object-Oriented and Conventional Process Automated Systems", 1994, 6 pages.

Thayer, Chem. Eng. News, Feb. 12, 1996 pp. 57-64.

Xiang et al., Science 268, (1995) 1738-1740.

Corkan et al., "Experiment Manager Software for an Automated Chemistry workstation, Including a Scheduler for Parallel Experimentation," Chemometrics and Intelligent Lab. Sys., vol. 17, 1992, pp. 47-74.

Thayer, "Bioinformatics for the Masses, (http://pubs.acs.org/hotartcl/cenear/000207/7806bus1.html)", Accessed on Mar. 22, 2000, Business, 2000, vol. 78(6), pp. 19-32.

McFarland et al., "Approaches for Rapid Materials Discovery Using Combinatorial Methods," Matrice Technologies, Ltd., vol. 13.3, 1998, pp. 107-120.

Cargill et al., "Automated Combinatorial Chemistry on Solid Phase," LRA, vol. 8, 1996, pp. 139-148.

Grigoriadis et al., "A Relational System for Managing High-Throughput Screening Data," Application Note, vol. Apr. 1997, pp. 53-54.

Network Science, "Introducing MDL Screen," (www.netsci.org/Schience/Screening/feature03.html), Website, Nov. 15, 2002, 4 pages.

MDL Information Syst., "MDL Screen 1.3 Closes Final Gap in HTS Workflow," 1998, 8 pages.

Afferent Systems Inc., "Afferent Analytical," website, Jan. 28, 1999, 1 page.

Afferent Systems Inc., "What's New? IRORI and Afferent Enter Into Combinatorial chemistry Collaboration Agreement," website, Jul. 3, 1999, 2 pages.

U.S. Appl. No. 09/174,856, filed Oct. 19, 1998, Lacy et al.

U.S. Appl. No. 11/325,267, filed Jan. 3, 2006, Falcioni et al.

U.S. Appl. No. 12/482,353, filed Jun. 10, 2009, Barstow.

Barr, R.S. et al., "Designing and reporting on computational experiments with heuristic methods", Journal of Heuristics Kluwer Academic Publishers Netherlands, vol. 1, No. 1 (Sep. 1995), pp. 9-32.

\* cited by examiner

```xml
<NameValueDefinition ID="1" ConCheck="0" PersistState="0">
    <Project>Polymer Formulation</Project>
    <DataName>VisualInspectionImage</DataName>
    <DataType>32</DataType>
    <DisplayName>Camera image</DisplayName>
    <Comments></Comments>
    <Required>1</Required>
    <ExperimentName>VisualInspection</ExperimentName>
    <Scope>2</Scope>
</NameValueDefinition>

<NameValueDefinition ID="2" ConCheck="0" PersistState="0">
    <Project> Polymer Formulation </Project>
    <DataName>VisualInspectionComment</DataName>
    <DataType>1</DataType>
    <DisplayName>Content notes</DisplayName>
    <Comments></Comments>
    <Required>0</Required>
    <ExperimentName>VisualInspection</ExperimentName>
    <Scope>2</Scope>
</NameValueDefinition>
```

*FIG. 4A*

| NAMEVALUEDEFINITION | | |
|---|---|---|
| PK | ID | NUMBER(11) |
| | PROJECT | VARCHAR2(80) |
| | DATANAME | VARCHAR2(240) |
| | DATATYPE | NUMBER(11) |
| | DISPLAYNAME | VARCHAR2(240) |
| | COMMENTS | VARCHAR2(4000) |
| | REQUIRED | BOOLEAN |
| | EXPERIMENTNAME | VARCHAR2(240) |
| | SCOPE | NUMBER(11) |

*FIG. 4B*

```xml
- <NameValueExperiment ID="42" ConCheck="0" PersistState="0">
    <Staff>jchemist</Staff>
    <Status>0</Status>
    <Comment>Manual sample screening</Comment>
    <Project>Testing</Project>
    <Notebook>1033</Project>
    <Pages>16C3</Pages>
    <Flags>0</Flags>
    <LibRows>1</LibRows>
    <LibCols>3</LibCols>
    <Log></Log>
    <LibID>133000</LibCols>
    <ExperimentName>VisualInspection</ ExperimentName>
    <NameValueElements>
        <NameValueElement ID="0" Concheck="0" PersistState="0">
            <Position>1</Position>
            <Flags>0</Flags>
            <Comments></Comments>
            <Name>VisualInspectionImage</Name>
            <ImageID>54</ImageID>
            <Status>0</Status>
        </NameValueElement>
        <NameValueElement ID="0" Concheck="0" PersistState="0">
            <Position>1</Position>
            <Flags>0</Flags>
            <Comments></Comments>
            <Name>VisualInspectionComment</Name>
            <SValue>white powder</SValue>
            <Status>0</Status>
        </NameValueElement>
        <NameValueElement ID="0" Concheck="0" PersistState="0">
            <Position>2</Position>
            <Flags>0</Flags>
            <Comments></Comments>
            <Name>VisualInspectionImage</Name>
            <ImageID>55</ImageID>
            <Status>0</Status>
        </NameValueElement>
        <NameValueElement ID="0" Concheck="0" PersistState="0">
            <Position>2</Position>
            <Flags>0</Flags>
            <Comments></Comments>
            <Name>VisualInspectionComment</Name>
            <SValue>no solid</SValue>
            <Status>0</Status>
        </NameValueElement>
        <NameValueElement ID="0" Concheck="0" PersistState="0">
            <Position>3</Position>
            <Flags>0</Flags>
            <Comments></Comments>
            <Name>VisualInspectionImage</Name>
            <ImageID>56</ImageID>
            <Status>0</Status>
        </NameValueElement>
        <NameValueElement ID="0" Concheck="0" PersistState="0">
            <Position>3</Position>
            <Flags>0</Flags>
            <Comments></Comments>
            <Name>VisualInspectionComment</Name>
            <SValue>clear gel</SValue>
            <Status>0</Status>
        </NameValueElement>
</NameValueExperiment>
```

| Experiment Table | | | | | | |
|---|---|---|---|---|---|---|
| ID | LibID | ClassName | SubClassName | Staff | Status | Notebook |
| 40 | 133000 | Synthesis | | jchemist | 0 | 1033 |
| 42 | 133000 | NameValueExperiment | VisualInspection | jchemist | 0 | 1033 |

FIG. 6A

| Value Table | | | | | | | | | | |
|---|---|---|---|---|---|---|---|---|---|---|
| ID | ExpID | Position | Name | SValue | N | B | D | XY | ImageID | F |
| 1 | 42 | 1 | VisualInspectionImage | | | | | | 54 | |
| 2 | 42 | 1 | VisualInspectionComment | white powder | | | | | | |
| 3 | 42 | 2 | VisualInspectionImage | | | | | | 55 | |
| 4 | 42 | 2 | VisualInspectionComment | no solid | | | | | | |
| 5 | 42 | 3 | VisualInspectionImage | | | | | | 56 | |
| 6 | 42 | 3 | VisualInspectionComment | clear gel | | | | | | |

| Library ID | Row | Column | Name | String Value | N | B | D | XY | Image | F |
|---|---|---|---|---|---|---|---|---|---|---|
| 133000 | A | 1 | Camera image | | | | | | [picture] | |
| 133000 | A | 1 | Content notes | white powder | | | | | | |
| 133000 | A | 2 | Camera image | | | | | | [picture] | |
| 133000 | A | 2 | Content notes | no solid | | | | | | |
| 133000 | A | 3 | Camera image | | | | | | [picture] | |
| 133000 | A | 3 | Content notes | clear gel | | | | | | |

*FIG. 8A*

| Library ID | Row | Column | ~~Name~~ | (String Value) | ~~N~~ | ~~B~~ | ~~D~~ | ~~XY~~ | (Image) | ~~F~~ |
|---|---|---|---|---|---|---|---|---|---|---|
| 133000 | A | 1 | Camera image | | | | | | [picture] | |
| 133000 | ~~A~~ | ~~1~~ | Content notes | white powder | | | | | | |
| 133000 | A | 2 | Camera image | | | | | | [picture] | |
| 133000 | ~~A~~ | ~~2~~ | Content notes | no solid | | | | | | |
| 133000 | A | 3 | Camera image | | | | | | [picture] | |
| 133000 | ~~A~~ | ~~3~~ | Content notes | clear gel | | | | | | |

*FIG. 8B*

| Library ID | Row | Column | Camera image | Content notes |
|---|---|---|---|---|
| 133000 | A | 1 | [picture] | white powder |
| 133000 | A | 2 | [picture] | no solid |
| 133000 | A | 3 | [picture] | clear gel |

*FIG. 8C*

USER-CONFIGURABLE GENERIC EXPERIMENT CLASS FOR COMBINATORIAL MATERIAL RESEARCH

CROSS REFERENCE TO RELATED APPLICATIONS

This is a continuation of U.S. Ser. No. 10/351,466, filed on Jan. 24, 2003, now issued as U.S. Pat. No. 7,213,034, which is incorporated by reference in its entirety and which is the basis of a claim of priority under 35 U.S.C. §120.

BACKGROUND

This invention relates to database systems and methods for storing and manipulating experimental data.

The discovery of new materials with novel chemical and physical properties often leads to the development of new and useful technologies. Traditionally, the discovery and development of materials has predominantly been a trial and error process carried out by scientists who generate data one experiment at a time. This process suffers from low success rates, long time lines, and high costs, particularly as the desired materials increase in complexity. There is currently a tremendous amount of activity directed towards the discovery and optimization of materials, such as superconductors, zeolites, magnetic materials, phosphors, catalysts, thermoelectric materials, high and low dielectric materials and the like. Unfortunately, even though the chemistry of extended solids has been extensively explored, few general principles have emerged that allow one to predict with certainty the composition, structure and/or reaction pathways for the synthesis of such solid state materials.

As a result, the discovery of new materials depends largely on the ability to synthesize and analyze large numbers of new materials. Given approximately 100 elements in the periodic table that can be used to make compositions consisting of two or more elements, an incredibly large number of possible new compounds remain largely unexplored, especially when processing variables are considered. One approach to the preparation and analysis of such large numbers of compounds has been the application of combinatorial chemistry.

In general, combinatorial chemistry refers to the approach of creating vast numbers of compounds by reacting a set of starting chemicals in all possible combinations. Since its introduction into the pharmaceutical industry in the late 1980s, it has dramatically sped up the drug discovery process and is now becoming a standard practice in that industry (Chem. Eng. News Feb. 12, 1996). More recently, combinatorial techniques have been successfully applied to the synthesis of inorganic materials (G. Briceno et al., SCIENCE 270, 273-275, 1995 and X. D. Xiang et al., SCIENCE 268, 1738-1740, 1995). By use of various surface deposition techniques, masking strategies, and processing conditions, it is now possible to generate hundreds to thousands of materials of distinct compositions per square inch. These materials include high $T_c$ superconductors, magnetoresistors, and phosphors.

Using these techniques, it is now possible to create large libraries of diverse compounds or materials, including biomaterials, organics, inorganics, intermetallics, metal alloys, and ceramics, using a variety of sputtering, ablation, evaporation, and liquid dispensing systems as disclosed in U.S. Pat. Nos. 5,959,297, 6,004,617 and 6,030,917, which are incorporated by reference herein.

The generation of large numbers of new materials presents a significant challenge for conventional analytical techniques. By applying parallel or rapid serial screening techniques to these libraries of materials, however, combinatorial chemistry accelerates the speed of research, facilitates breakthroughs, and expands the amount of information available to researchers. Furthermore, the ability to observe the relationships between hundreds or thousands of materials in a short period of time enables scientists to make well-informed decisions in the discovery process and to find unexpected trends. High throughput screening techniques have been developed to facilitate this discovery process, as disclosed, for example, in U.S. Pat. Nos. 5,959,297, 6,030,917 and 6,034,775, which are incorporated by reference herein.

The vast quantities of data generated through the application of combinatorial and/or high throughput screening techniques can easily overwhelm conventional data acquisition, processing and management systems. Existing laboratory data management systems are ill-equipped to handle the large numbers of experiments required in combinatorial applications, and are not designed to rapidly acquire, process and store the large amount of data generated by such experiments, imposing significant limitations on throughput, both experimental and data processing, that stand in the way of the promised benefits of combinatorial techniques.

SUMMARY

The invention provides methods, systems and apparatus, including computer program apparatus, representing a generic experiment model or class adaptable to a researcher-defined set of variables, for processing data from chemical experimentation.

In general, in one aspect, the invention provides methods and apparatus, including computer program products implementing techniques for processing experimental data according to an object model. The techniques include receiving input specifying a first set of one or more variable definitions according to a variable definition template for defining variables of a plurality of variable types, receiving data from an experiment of a first experiment type, storing a first representation of the data from the experiment of the first experiment type in a format defined according to the plurality of variable types, and presenting a second representation of the data from the experiment of the first experiment type in a format defined according to the first set of variable definitions. The variable definition template is referenced in a first pre-defined experiment class of the object model. The plurality of variable types are usable in experiments of the first pre-defined experiment class. The first set of variable definitions defines a set of variables of one or more of the plurality of variable types for the first experiment type. The data includes a plurality of values corresponding to variables defined in the first set of variable definitions. The second representation of the data from the experiment of the first experiment type is derived from the first representation.

Advantageous implementations can include one or more of the following features. The input specifying a first set of one or more variable definitions can include input defining an experiment name and, for each variable in the set of variable definitions, input defining a variable name and a datatype. The first representation can include an entry for each of the plurality of values. The second representation can include an entry representing values for two or more variables defined in the first set of variables. Each entry can be a row in a table. The data from the experiment of the first experiment type can include values for a plurality of members of a library of materials. The second representation can include an entry representing values for two or more variables for a member of the library. The first representation can be a sparse table. The second representation can be a dense table. The second representation can include columns corresponding to the defined variables.

A set of data from a second experiment can be received. The second set of data can include one or more values corresponding to a set of variables defined in a second pre-defined experiment class of the object model. A representation of the data from the experiment of the second experiment type can be stored and presented in a format defined according to the second pre-defined experiment class of the object model.

Input can be received specifying a second set of one or more variable definitions according to the variable definition template. The second set of variable definitions can define a set of variables for a second experiment type. Data can be received from an experiment of the second experiment type. The data can include a plurality of values corresponding to variables defined in the second set of variable definitions. A first representation of the data from the experiment of the second experiment type can be stored in a format defined according to the variable definition template. A second representation of the data from the experiment of the second experiment type can be presented. The second representation can be derived from the first representation and presented in a format defined according to the second set of variable definitions.

The invention can be implemented to realize one or more of the following advantages. The class is user-configurable. The class can be dynamically extended to include additional sets of variables without additional server or database software development. The configuration is accomplished by the definition of variables. The variables can be defined by the researcher. The experimental results are presented for querying and viewing in an equivalent manner as for non-configurable or pre-defined experiments. Instances of the generic experiment class can be used to extend an object model that also implements specific classes. The class provides a rapid and accessible data storage method. The class is suitable for low to medium volumes of data with minimal software development requirements.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 5A-5B illustrate an XML document defining a user-configured experiment object and the relational database tables into which the object is mapped.

Like reference symbols in the various drawings indicate like elements.

DETAILED DESCRIPTION

Figure 1:
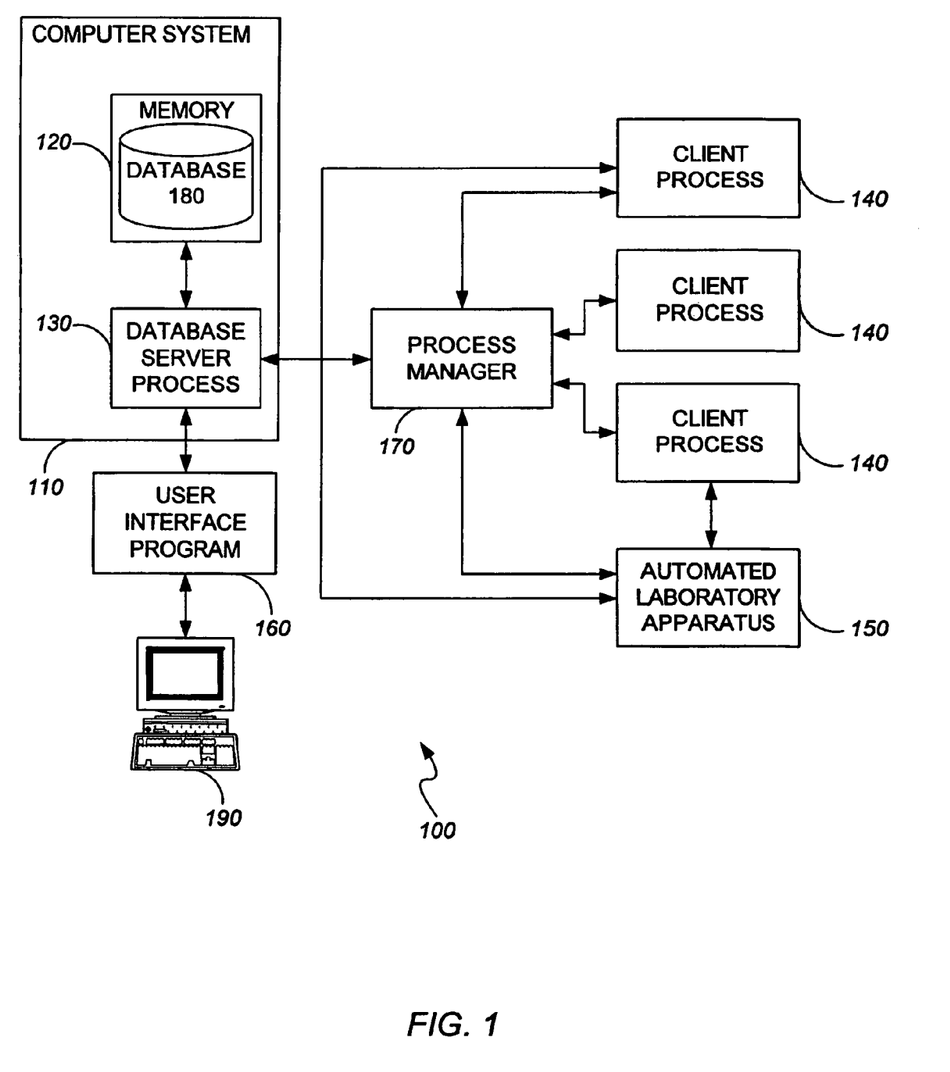
FIG. 1 is a block diagram illustrating a laboratory data management system including a database server process according to one aspect of the invention.

FIG. 1 illustrates a laboratory data management system 100 that includes a general-purpose programmable digital computer system 110 of conventional construction including a memory 120 and a processor for running a database server process 130, and one or more client processes 140. As used in this specification, a client process is a process that uses services provided by another process, while a server process is a process that provides such services to clients. Client processes 140 can be implemented using conventional software development tools such as Microsoft® Visual Basic®, C++, and Java™, and laboratory data management system 100 is compatible with clients developed using such tools. In one implementation, database server process 130 and client processes 140 are implemented as modules of a process control and data management program such as that described in U.S. application Ser. No. 09/550,549, filed Apr. 14, 2000, which is incorporated by reference herein. Optionally, client processes 140 include one or more of automated or semi-automated laboratory apparatuses 150, a user interface program 160 and/or a process manager 170 for controlling laboratory apparatus 150. Exemplary laboratory apparatuses, user interface programs and process managers are described in more detail in U.S. application Ser. No. 09/239,223, filed Jan. 1, 1999, and U.S. application Ser. No. 09/550,549, filed Apr. 14, 2000, each of which are incorporated by reference herein.

Laboratory data management system 100 is configured to manage data generated during the course of the experiments. Database server process 130 is coupled to a database 180 stored in memory 120. In general, laboratory data management system 100 receives data from client 140 for storage, returns an identifier for the data, provides a way of retrieving the data based on the identifier, provides the ability to search the data based on the internal attribute values of the data, and the ability to retrieve data from the these queries in a number of different ways, generally in tabular (e.g., in a relational view) and object forms. In one implementation, laboratory data management system 100 maintains three representations of each item of data: an object representation; a self-describing persistent representation, and a representation based on relational tables. Laboratory data management system 100 can be implemented as a laboratory information system as is described in U.S. application Ser. No. 09/755,623, filed Jan. 5, 2001, which is incorporated by reference herein.

Experiments are performed, for example, by laboratory apparatus 150, on an experimental sample such as a single material or, more typically, on a set of experimental samples such as a library of materials. A library of materials is a collection of members, typically two or more members, generally containing some variance in chemical or material composition, amount, reaction conditions, and/or processing conditions. The library can be a matrix, where each member represents a single constituent, location, or position on a substrate. The library can be a conceptual collection, where each member represents, for example, data or analyses resulting from the analysis of experiments performed on unrelated samples (e.g., samples that are not located on a common substrate), or from simulations or modeling calculations performed on hypothetical samples. Experiments can involve the measurement of numerous variables or properties by the laboratory apparatus, as well as processing (or reprocessing) data gathered in previous experiments or otherwise obtained, such as by simulation or modeling. Typical laboratory apparatus and experimental data suitable for use in and/or manipulation by the laboratory data management systems described herein are, discussed in more detail in U.S. application Ser. No. 09/755,623, filed Jan. 5, 2001, and U.S. application Ser. No. 09/840,003, filed Apr. 19, 2001.

Database 180 stores experimental data, including observations, measurements, calculations, and analyses of data from experiments performed by laboratory data management system 100. In one implementation, data is stored as a series of values, each having one of potentially several types. "Name" refers to a property of a material or, more generally, an experimental variable. "Value" refers to data that are associated with a named variable. The data can be one of many possible data types, and can be observed, measured, calculated, or otherwise derived for the experiment. The data can be, for example, a number, a phrase, a data set, or an image. The data can be for the entire library or for individual member elements of a library. In the former case, one or more values can be represented corresponding to one or more substrates in their entirety, for example an image of the entire substrate. In the latter case, data can be collected for each element or for any set of elements. The data can include multiple measurements for any given element or elements, as when measurements are repeated or when multiple measurements are made, for example, at different set points, different locations within a given element or elements, or at different times during the experiment. For example, the optical reflectance of the material at each element position can be measured at multiple wavelengths, and each measurement can be repeated for accuracy within the same experiment.

Figure 2A:
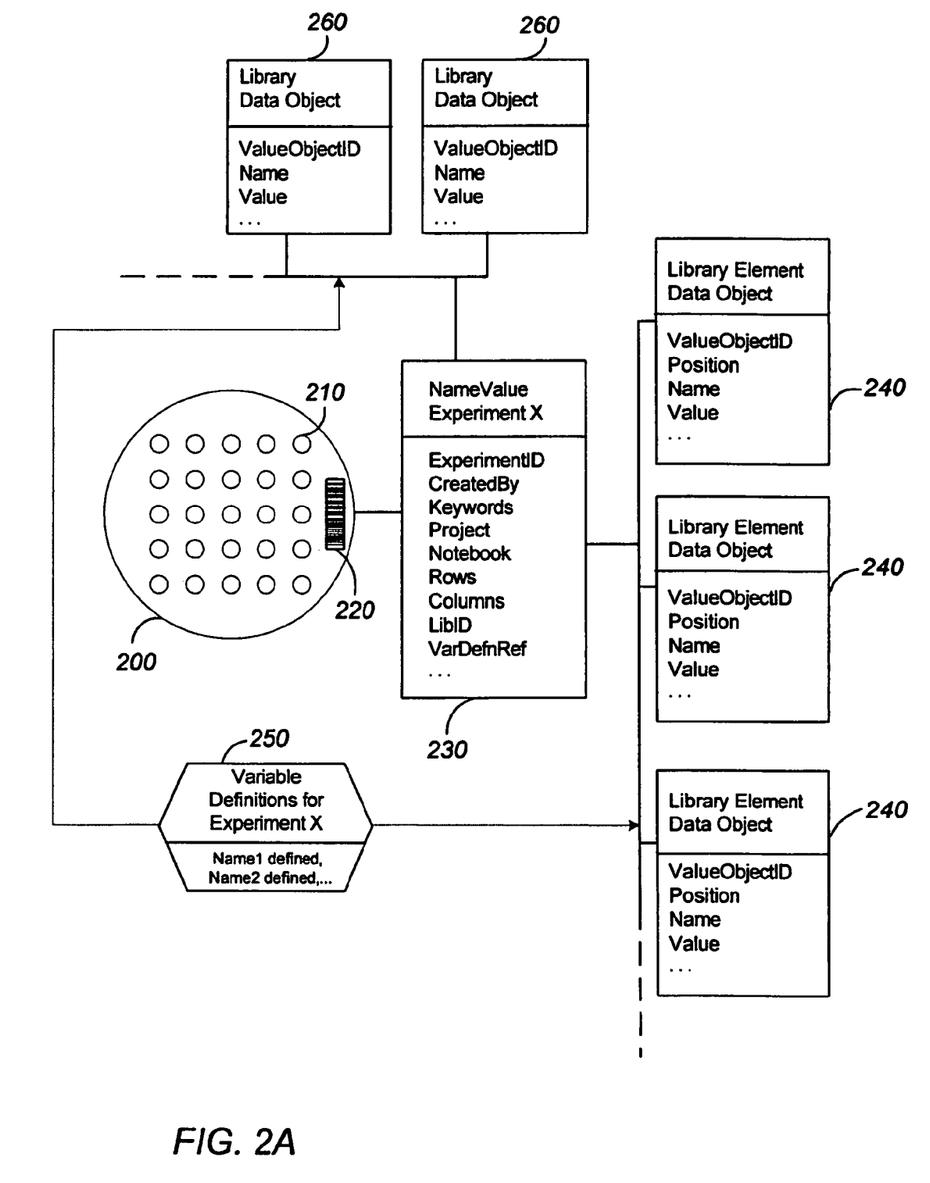
FIG. 2A is a diagram illustrating an object model implementing a user-configurable generic experiment class according to one aspect of the invention.

In one implementation, client processes 140 interact with experimental data generated in system 100 through an object model representing an experiment performed by system 100, as illustrated in FIG. 2A. In this object model, an experiment performed by system 100 is represented by an experiment object 230—here referred to as a NameValueExperiment—having a set of associated properties and methods that represent the experiment. The experiment object 230 can be associated with a particular library of materials 200—for example, by virtue of an associated LibraryID 220 (here represented as a barcode) that identifies the library in laboratory data management system 100. The experiment object 230 is also associated with Library Element Data Objects 340, which are typically children of the experiment object 230.

The Library Data Objects 260 and Library Element Data Objects 240 identify data for experimental properties or variables ("names") 250 defined by the user, as will be described in more detail below. If the experiment involves multiple members of a library, there is typically a Library Element Data Object for each named variable 350 for each member or position 310 of the library 300. There can be Library Element Data Objects for only some of the defined variables at some of the members of the library. For example, values for a comment variable can be defined only for interesting or notable members of the library. The data typically does not include values of undefined types or for undefined variables. Similarly, Library Data Objects 260 are associated with the library 200. Each Library Data Object 260 can include data for the library as a whole or for a subset of members of the library.

In one implementation, the user-configurable generic experiment object 230 can be implemented in an object model that implements a user-configurable generic experiment class and one or more specific experiment classes configured to represent data for particular experiment types. Thus, for example, the user-configurable generic experiment class can be implemented as a subclass of an experiment base class, and can inherit from the base class general properties associated with an experiment, such as ExperimentID, an integer uniquely identifying the experiment within system 100; Keywords, strings specifying searchable terms identifying the experiment; Project, a string describing the context or motivation for the newly defined experiment; Notebook, an integer identifying the laboratory notebook in which the experiment is recorded; LibRows and LibCols, integers identifying the number of rows and columns in the relevant library; and the like. To this set of general inherited properties, the user-configurable generic experiment (sub)class adds a reference to a set of variable definitions, such as the name of the experiment for which the experimental variables have been defined. Typically, the named reference can be instantiated to provide one or more Variable Definition Objects. The user-configurable generic experiment (sub)class can also add a collection of Library Data Objects and/or a collection of Library Element Data Objects. The Library Data Objects can contain data applicable to the entire library under study, and typically are defined by the Variable Definitions. The Library Element Data Objects, which also typically are defined by the Variable Definitions, can contain data applicable to each or any of the individual elements of the library.

Figure 2B:
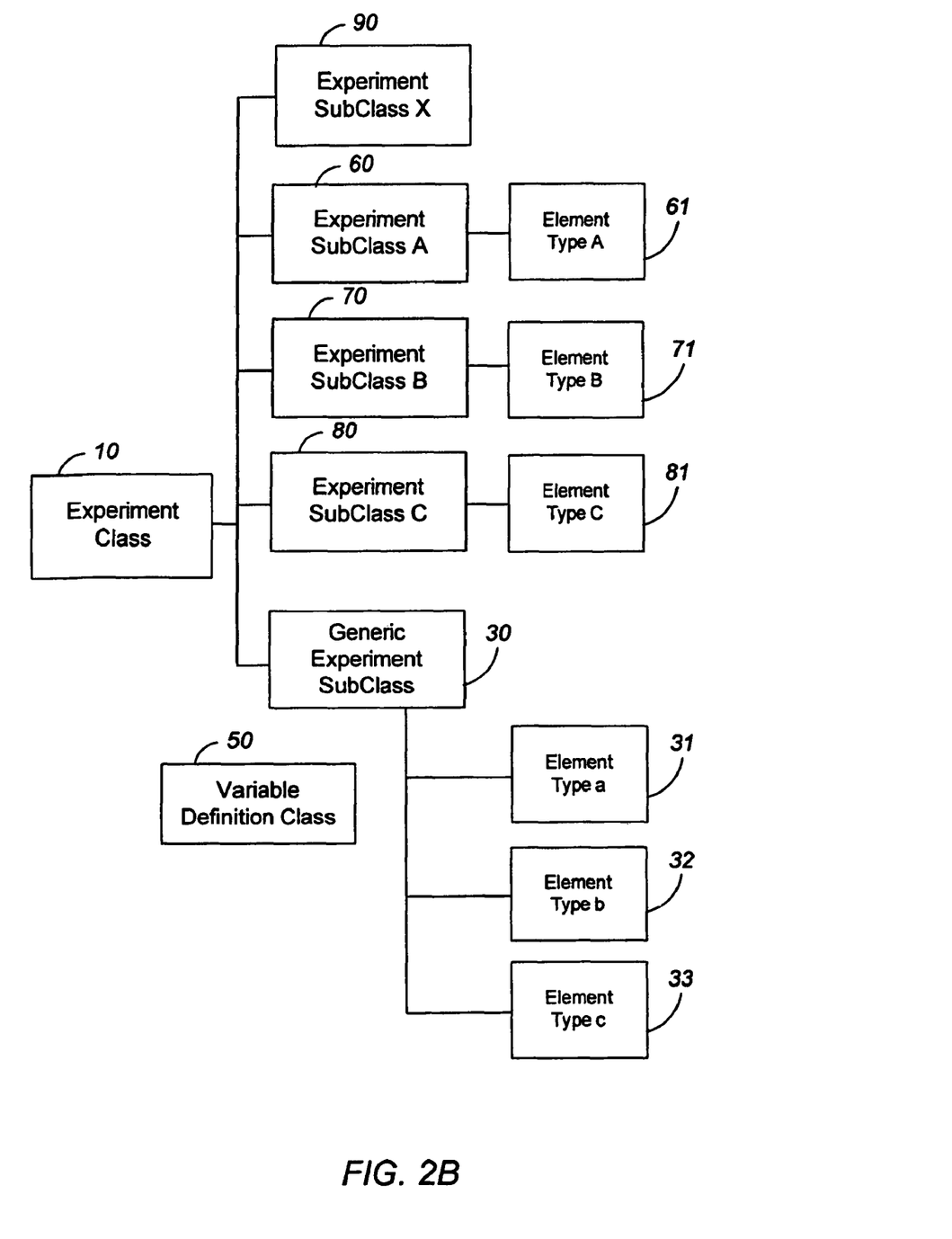
FIG. 2B is a diagram illustrating a user-configurable generic experiment subclass according to one aspect of the invention and several specific experiment subclasses.

The form of a particular experiment object 230 is dependent upon the associated definition 250 of the properties of Library Element Data Objects 240 and the Library Data Objects 260. As shown in FIG. 2B, a generic experiment subclass 30 can be derived from or inherit the properties of an experiment class 10. Similarly, various specific experiment subclasses 60, 70, 80, can be derived from or inherit the properties of the experiment class 10. Each instantiation of a specific experiment subclass 60, 70, 80, typically defines a different kind of experiment and can be associated with a particular type of elements 61, 71, 81, which refer to the data for the experiment. For example, a gel permeation chromatography (GPC) experiment subclass would have elements with properties specifically defined to receive data of the type generated in GPC experiments, such as molecular weight and it's moments Mw, Mn, and Mz, and polydispersity index PDI, as described in U.S. application Ser. No. 09/755,623, filed Jan. 5, 2001.

An instantiation of a user-configurable generic experiment subclass 30 can be associated with one or more of many possible definitions of elements 31, 32, 33, depending upon the instantiation of the Variable Definition Class 50. Because each instance of the user-configurable generic experiment subclass 30 can differ from other instances according to the variable definitions on which its Library Data Objects and Library Element Data Objects are based, the Variable Definition Class 50 can be used to effectively define a variety of different "virtual subclasses" by defining elements that are instantiated as objects that can, for example, represent different types of experiments as would specific experiment objects instantiated from different pre-defined subclasses 60, 70, 80, of the experiment class 10.

Figure 3:
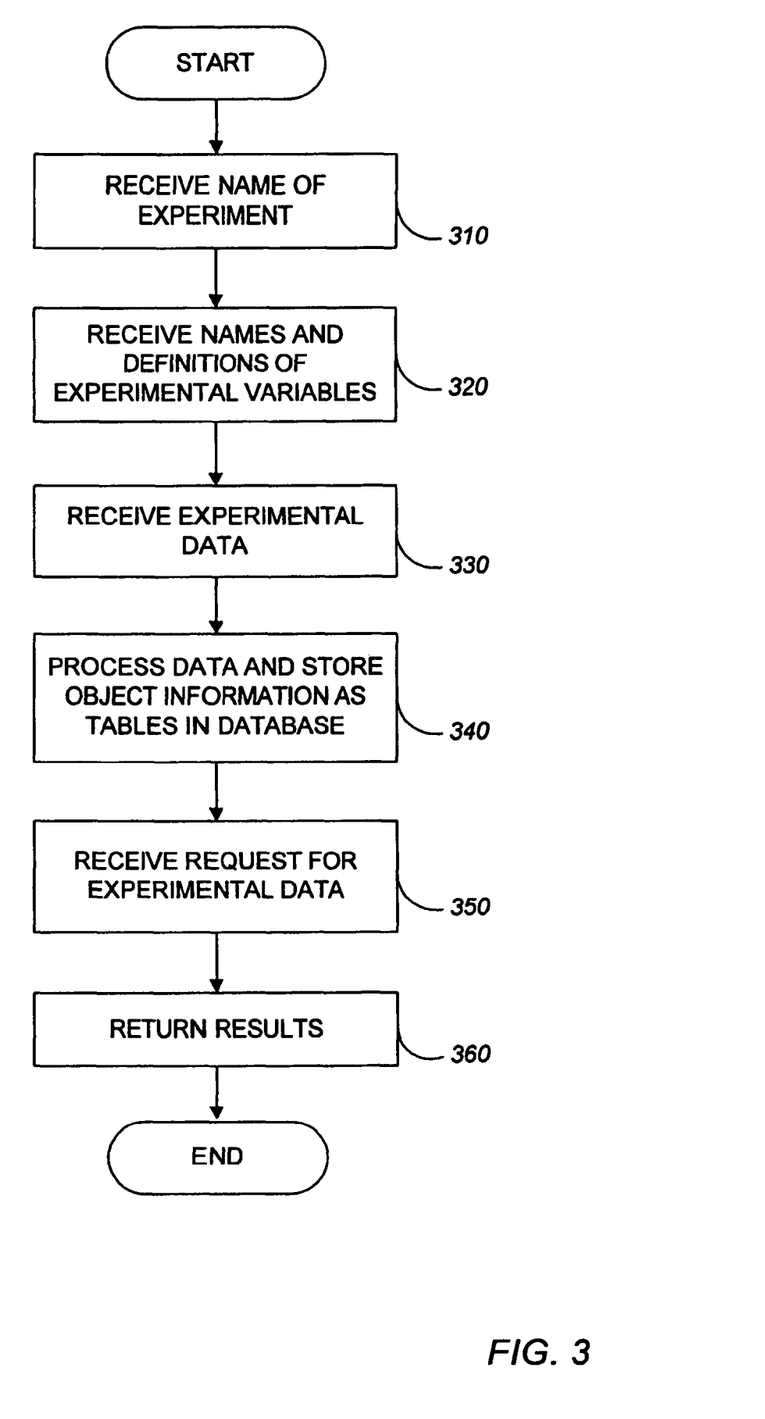
FIG. 3 is a flow diagram illustrating a method of defining an experiment as a subclass of a user-configurable generic experiment class according to one aspect of the invention.

The object model shown in FIGS. 2A-B can be used as shown in FIG. 3. A new experimental model or "experiment" is created by defining the variables for the user-configurable generic experiment class. The variables can be defined by the researcher, for example, using a GUI. System 100 receives a name for the experiment (step 310). The name must uniquely identify the set of variables to be defined and is typically a string, for example, "VisualInspection". System 100 receives the names of properties or variables to be included in the experiment, and an indication of the data type of each named variable (step 320). Each variable can have two or more names, for example, a variable can have a data name, used in data storage, and a display name, used when displaying the data to the researcher. The data type can be one of many types, including string, double, date, boolean, XYDataset, image, and external data file. In one implementation, the data type for each named variable can be selected in step 320 from a predefined set of data types corresponding to the range of data types needed to represent data from experiments that can be performed using laboratory data management system 100. Additional information that can be used in a GUI for data entry system 100, can be associated with the name, for example, comments that include descriptive information about the field, and a flag indicating whether a value for the data name is required to complete the experiment.

System 100 receives experimental data (step 330), typically in the form of data objects, and processes the data for storage in the database 180 (step 340). In one implementation, database server process 130 maps classes (e.g., an experiment subclass 60, 70, 80, or the user-configurable generic class 30) to database tables, with each row representing an individual instance of the class or classes in the table, as described in more detail below. Communication between client processes 140 and database server process 130 using data objects, and the extraction and storage of data in relational database tables are described in more detail in U.S. application Ser. No. 09/755,623, filed Jan. 5, 2001. After data are stored, system 100 can then receive a request for stored experimental data (step 350), and can return the requested data to the user (step 360).

As an example, a "visual inspection" experiment can involve monitoring the visual attributes of a particular reaction, with the visual attributes being recorded as images of the material or materials over the course of the experiment and notes about their visual appearance. Such an experiment can be implemented in system 100 by creating a specific subclass 60, 70, 80 of an Experiment base class 10, e.g., as described in U.S. application Ser. No. 09/755,623, filed Jan. 5, 2001. The definition of a specific experiment subclass can require a level of expertise and effort that is appropriate or justified for high-volume experiments or experiments conducted repeatedly.

A "visual inspection" experiment also can be implemented using the pre-defined, user-configurable generic experiment class as described herein; the visual inspection experiment is defined by defining the variables for a particular instance of the user-configurable generic experiment class. For example, a researcher creates a visual inspection experiment by defining, for example, an image variable that takes image data, and a notes variable that takes string data. The definition of variables for a user-configurable generic experiment class can require minimal expertise and effort, such that this approach can be used for low-volume or uncommon or atypical experiments, such as pilot, exploratory, or scale-up experiments.

Figure 4A:
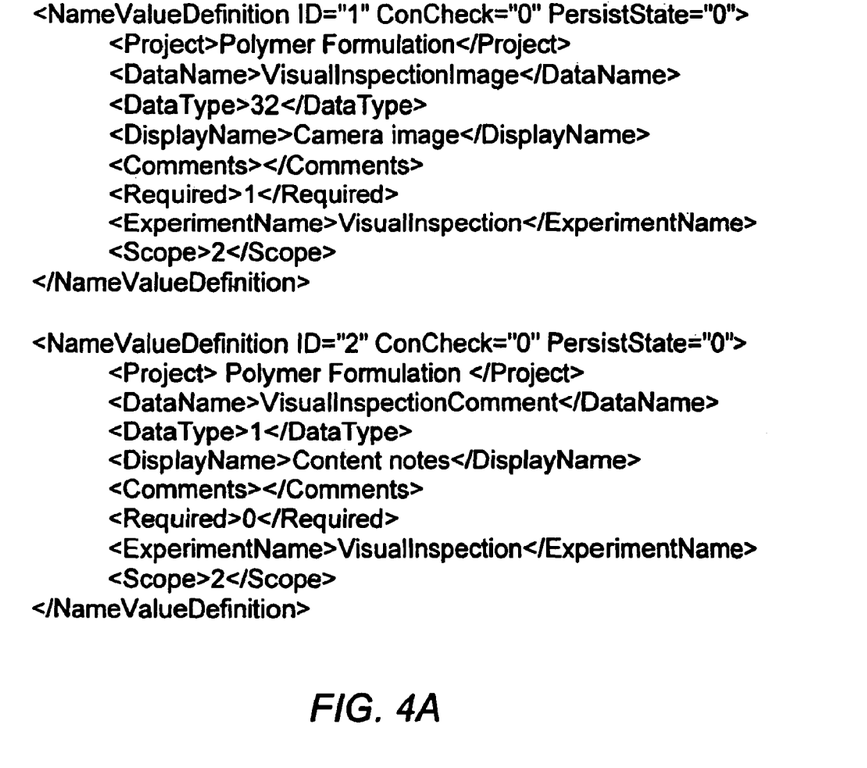
FIGS. 4A-4B illustrate XML documents defining variables and the relational database table into which such an object is mapped.

Variables of a user-configurable generic experiment class can be defined, for example, using a GUI to create variable definition objects, for example, as XML code. A wizard can be used to prompt the user to provide the information necessary to create the variable definition objects. For example, a wizard can prompt the user for a name of the experiment and then prompt the user for information for each variable, for example, by displaying the variable's DataName and Description and, based on the variable's DataType, providing data type checking or other use aids. For example, a standard system file browser can be used to select an external file in the case of a Variable of StoredFile type. The wizard then converts the information received into XML. In one implementation, variable definition objects can also be defined automatically, for example, based upon one or more sample data sets. The sample data set can be parsed to identify variables in the data, and a variable definition for each variable type can be generated—for example, by extracting relevant attributes of the corresponding data (e.g., attributes of a corresponding element defined in an XML stream representing the sample data set). FIG. 4A illustrates a portion of an XML document representing two variable definition objects—denoted here as NameValueDefinition Objects—for an experiment having the name VisualInspection. Database server process 130 receives a variable definition object represented by the XML of FIG. 4A (step 230) and parses it into storage in an Oracle table whose format is shown in FIG. 4B (step 240).

In the example shown in FIG. 4A, the first variable definition object has ID="1" and defines an image variable representing an image of a library member. The variable is given two names: a DataName, "VisualInspectionImage," and a DisplayName, "Camera image." The DataName is used to reference the variable internally within system 100, while the DisplayName is use to present the values of the variable to the user. The data value to be associated with this name is of image data type, as shown by DataType=32 where 32 is a code for "image." Each DataName should be unique within the scope of the ExperimentName, and should have a DataType value chosen from a set of integers that represent a set of supported data types, such as string, double, date, Boolean, XYDataSet, Image, and StoredFile. Each variable definition object is denoted as having a library or library element scope, which defines whether the data is to be collected on the entirety of the library or on each or any library element. The Scope for the first variable definition object is the value 2, which denotes the data apply to the library elements. The Required value of 1 means that a valid image will be required of any experimental data to be stored.

The second variable definition object in FIG. 4A defines a "notes" variable representing textual observations resulting from a visual inspection of a library member (or a corresponding image). The variable is given two names: a DataName, "VisualInspectionComment," and a DisplayName, "Content notes." The data value to be associated with this name is of string data type, as shown by DataType=1 where 1 is a code for "string." The scope of the variable is also defined as 2, where 2 is the code for library element scope, as described above. Comments can be but are not included in this example. The Required value of 0 means that the data is optional.

Figure 4B:
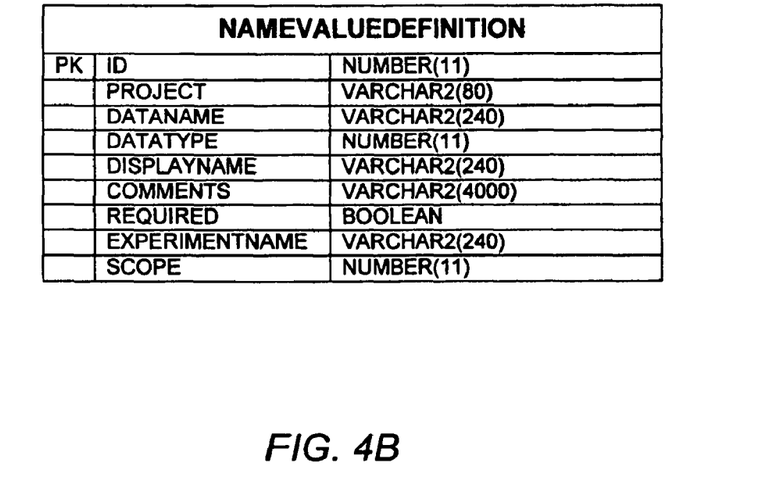

FIG. 5A illustrates an XML document that is received by the Database server process 130 (step 230) and represents data from the VisualInspection experiment having variables as defined in FIGS. 4A-B. The XML can include properties inherited from the Experiment base class. For example, the base class can define properties that generally describe any experiment that can be performed using the system, such as the name of the researcher creating or conducting the experiment, the notebook and pages where the experiment is recorded, and the identity of the library. The user-configurable generic experiment class can define properties such as the geometry of the library of materials, and, by name, the set of variable name definition objects that are used in this specific instance. In this example, the library has 1 row and 3 columns for a total of 3 members (libraries typically will but need not necessarily have more members), and the experiment is using variable definition objects defined for a "VisualInspection" experiment.

The XML representation of the visual inspection experiment can also include the Library Element Data Objects that represent the data for the experiment. Typically, there is a Library Element Data Object for each named variable at each position. In general, for an experiment of v variables and a library of p positions, there will be p×v Library Element Data Objects. (The number of positions can, for example, be determined from the number of rows, r, and columns, c, as p=r×c.) For a large library and an experiment having many variables or properties, the number of Library Element Data Objects can be very large. In some implementations it may be desirable to limit the number of Library Element Data Objects, and the number of variables, for a given experiment to limit the consumption of memory and/or processing resources.

In the example, there are 3 positions 310, as indicated in FIG. 5A, and 2 named variables 350, as indicated in FIG. 4A (VisualInspectionImage and VisualInspectionComment). Thus, there are 6 Library Element Data Objects, as shown in FIG. 5A. Each Library Element Data Object provides a value, in this case either ImageID (data type image) or SValue (data type string), for a variable at a given position. As shown, the first Library Element Data Object provides the ImageID for the picture at position 1, the second Library Element Data Object provides the SValue for the notes about position 1, the third Library Element Data Object provides the ImageID for the picture at position 2, the fourth Library Element Data Object provides the SValue for the notes about position 2, the fifth Library Element Data Object provides the ImageID for the picture at position 3, and the sixth Library Element Data Object provides the SValue for the notes about position 3. The specific values of certain data types typically are not stored or represented within the NameValueExperiment. For example, concrete instances of variable objects of DataType XYDataSet, Image, or StoredFile can be stored and represented as reference IDs, which refer to externally stored objects of these types.

Figure 5B:
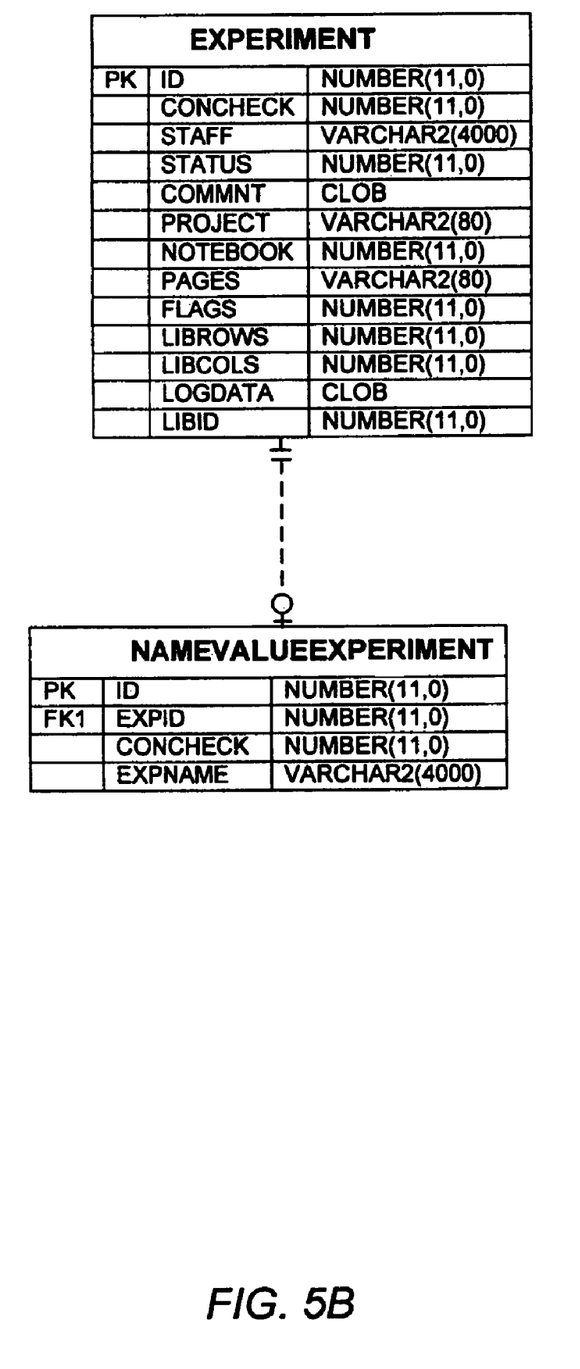

Database server process 130 maps the experiment object represented by the XML of FIG. 4A into one or more Oracle tables, for example, the tables whose format is shown in FIG. 5B (step 240).

Figure 6A:
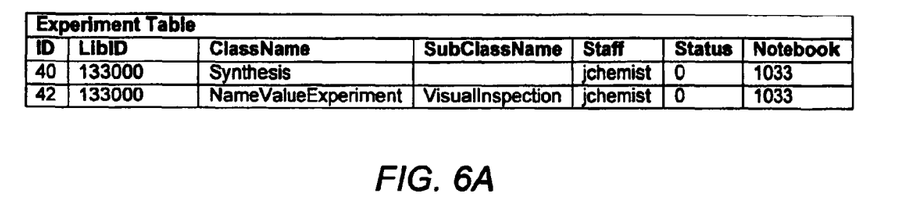
FIGS. 6A-6B illustrate relational database tables used to store data for a NameValueExperiment object for an exemplary experiment called VisualInspection.
Figure 6B:
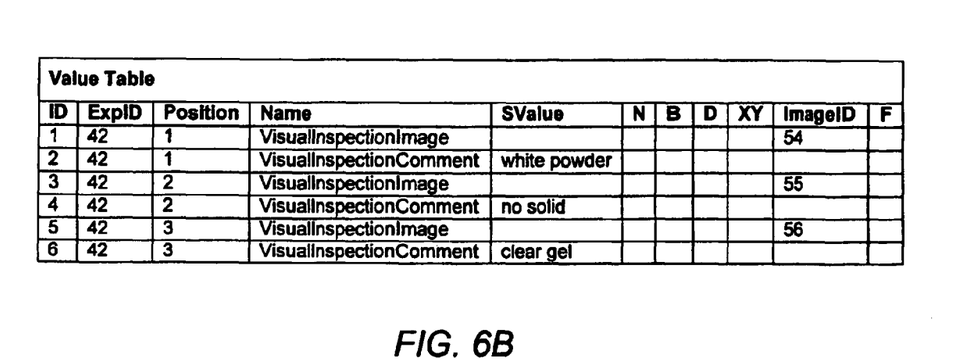

FIGS. 6A-B show the relational database tables for a library and a newly defined experiment on that library called VisualInspection, as was defined in FIG. 4A and as shown in FIG. 5A. Information about Experiment classes associated with the library used in the Visual Inspection experiment is shown in FIG. 6A. Included is an entry for a specific class called Synthesis and an entry for a user-configurable generic class called NameValueExperiment, for which a virtual subclass, VisualInspection, has been defined. Information from the Library Element Data Objects for the instantiation of the NameValueExperiment class as specified by the variable definitions for the experiment called VisualInspection is shown in FIG. 6B. There is an entry for each Library Element Data Object. In this example, each entry is a row and columns correspond to the data types that a value can take. Although a particular Library Element Data Object typically has only one value, the value can be one of many types (string or SValue, number or NValue, etc.). The Library Element Data Object Table is therefore sparse, having a large number of empty cells (i.e., cells having values that are zero or undefined). There are numerous columns, corresponding to the possible datatypes for a named variable, but for any given row, there is typically data in only one or a few of these columns.

A user of system 100 can search and/or retrieve data (step 250) from database 180. The overall process is the reverse of the process of storing objects: the system retrieves the object from the database, and maps into an XML document and the document is returned to the requester as a string. In general, clients and users are isolated from the details of data storage in database 180, and can only manipulate data in ways explicitly permitted by database server process 130. A user can, for example, submit requests by manipulating a menu bar in a Queries window displayed by a user interface program. Exemplary methods for searching and retrieving data are described in U.S. application Ser. No. 09/755,623, filed Jan. 5, 2001.

The system 100 typically presents the user with a tabular representation of requested object data. The tabular representation capability of the server provides access to data for multiple objects in a compact form resembling a single relational table. A user can select certain fields to be displayed and can otherwise manipulate the data to be presented. System 100 can then present a table having one or more rows corresponding to the objects satisfying the query, and one or more columns corresponding to the selected displayable fields. Exemplary methods for presenting data in a tabular form resembling a relational table are described in U.S. application Ser. No. 09/755,623, filed Jan. 5, 2001 and PCT application number PCT/US02/00466, filed Jan. 7, 2002, which is incorporated by reference herein.

Figure 8A:
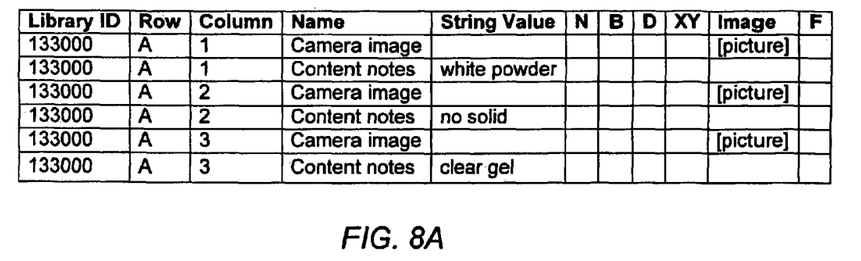
FIGS. 8A-8C illustrate the default user interface for viewing data retrieved from a experiment defined by a user-configured generic experiment class, the translation or pivoting of elements in the default user interface, and the resulting pivoted user interface for viewing data retrieved from the experiment.

Presentation of the data for a user-configurable generic experiment object as it is stored in the relational data base, as shown in FIG. 6B, may result in presentation of a sparse representation of the data, characterized by a multiplicity of data per library element in the vertical direction, as shown in FIG. 8A. Because the presentation of the data in this form requires a user to scan both horizontally and vertically through the data, and furthermore to correlate two columns of information in order to process what is essentially one relevant experimental fact, this presentation of the data can be both insufficient and undesirable from a user's point of view.

Figure 7:
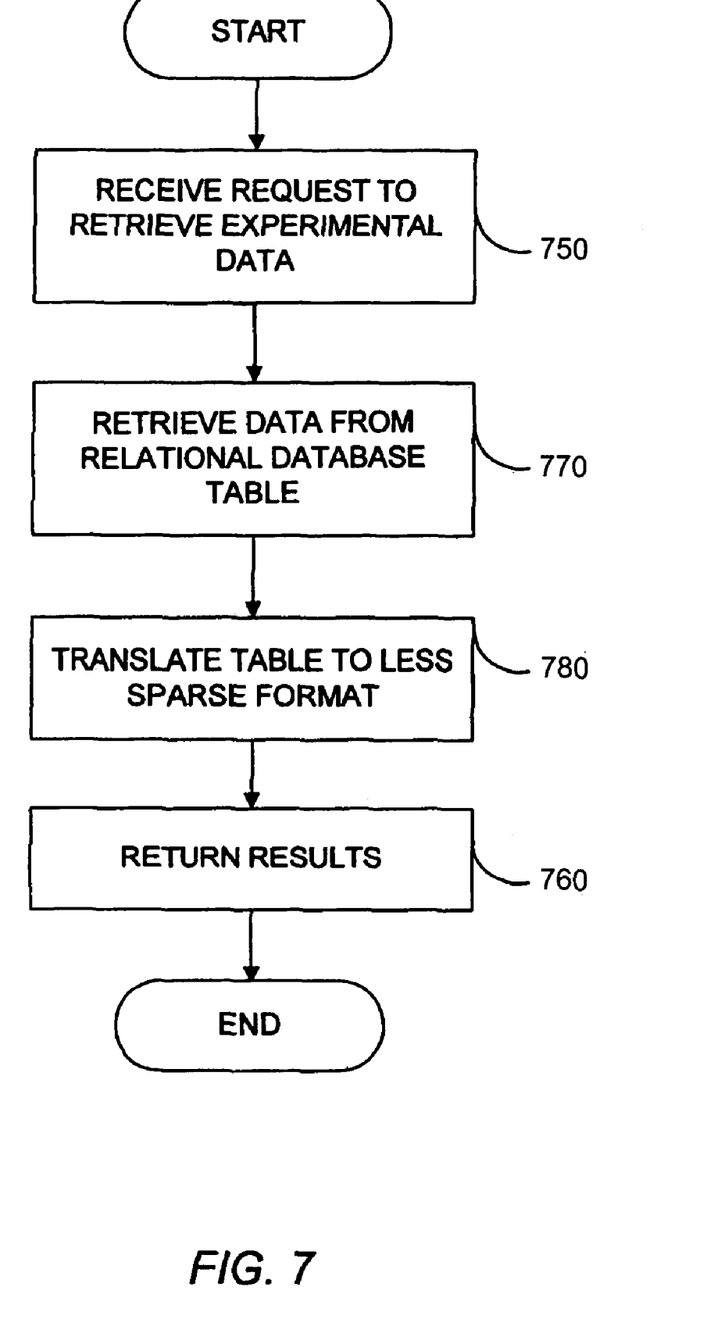
FIG. 7 is a flow diagram illustrating a method of presenting the results of an experiment defined as a subclass of a user-configurable generic experiment class according to one aspect of the invention.

In one implementation, the system 100 can translate the data table having requested data before returning the data to the user. As shown in FIG. 7, system 100 receives a request for experimental data (step 250). The system retrieves the data from a relational database table (step 270) and translates or pivots the data generating a dense representation of the data for presentation based on information in the corresponding variable definition objects (step 280), such that the empty data fields are removed and the verticality of the data is translated into a multiplicity of columns, where each column corresponds to a variable definition object. The results of the experiment are returned to the researcher as if the data storage were "column rich," which is the form generally used for other, specific types of derived experiment classes as described and shown by example in U.S. application Ser. No. 09/755,623, filed Jan. 5, 2001.

Figure 8B:
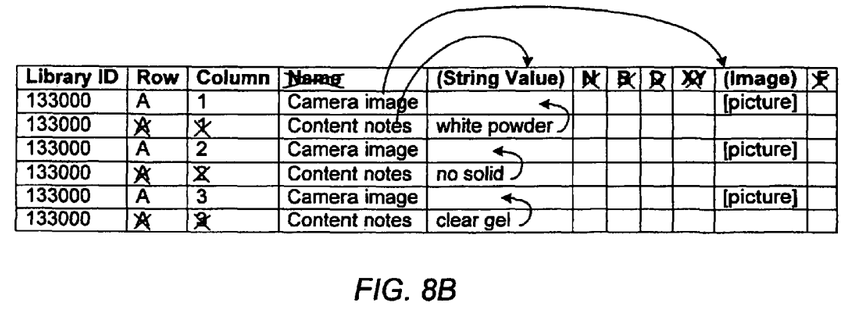
Figure 8C:
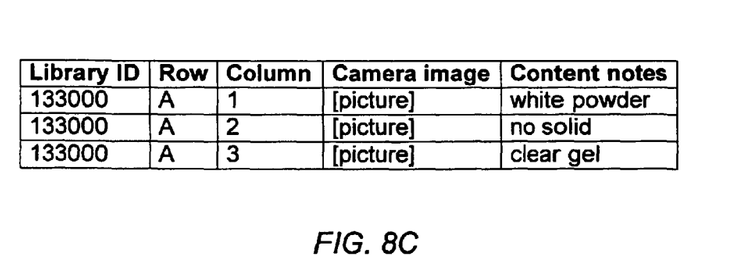

The generation of the dense representation is illustrated in FIGS. 8A-C. As shown in FIG. 8A, the default (sparse) representation of data from an experiment object resembles the Library Element Data Object table that is used to store the data (as shown in FIG. 6B). This representation includes an entry, for each Library Element Data Object. In this example, each entry is a row and columns correspond to the properties of the Library Element Data Object, including the variable's Name, and each of several possible data types for the value of that named variable, such as SValue, NValue, etc. While there is a column for each possible data type, typically only one column contains a reference to the particular object that contains the data. Because the value for a named property typically is of only one datatype, the table is sparse.

The default representation can be pivoted as shown in FIG. 8B to create a dense representation as shown in FIG. 8C. The name of each experimental variable is transposed to the head of column containing the values for that variable. For example, the variable whose DisplayName is "Camera image" has datatype "image." The column for the datatype, in this example, "image," is replaced with the DisplayName of the variable having that datatype, in this example, "Camera image." If there are two or more variables of the same datatype, then a separate column is created for each Variable.

After pivoting, the default representation can be collapsed to remove empty cells from the display. Data for some or all the variables at a single position in the library are then consolidated into a single entry, such as a row in a table. For example, the default representation shown in FIG. 8B includes two rows for the first position, row A and column 1, because there are two variables. To generate a dense representation, the values for all but one of the variables at this position, in this example, "Content notes," are combined in a single row. Columns without data are also removed from the display. The resulting pivoted and collapsed representation is shown in FIG. 8C. This representation includes a single entry or row for each position in the library, and a column for each named variable in the NameValueExperiment. Each cell contains a value for named variable at the indicated position.

A number of embodiments of the invention have been described. Nevertheless, it will be understood that various modifications may be made without departing from the spirit and scope of the invention. Accordingly, other embodiments are within the scope of the following claims.

What is claimed is:

1. A computer-implemented method for processing experimental data in a laboratory data management system according to an object model, the object model including a first pre-defined experiment class that is configured to be instantiated to define one or more experiment objects that represent data for particular experiments in the laboratory data management system, the method comprising:
  receiving, by a processor, input specifying a first set of one or more variable definition objects defining a set of variables for a first experiment type to be represented by the one or more instances of the first pre-defined experiment class, the variables in the set of variables having types selected from a predefined set of data types including attributes that are configured to be used to represent data for experiments in the laboratory data management system;
  receiving, by the processor, data for an experiment of the first experiment type, the data including a plurality of values corresponding to variables defined in the first set of one or more variable definition objects;
  storing a sparse representation of the data for the experiment of the first experiment type in a relational database table according to the set of types defined by the first set of one or more variable definition objects; and
  presenting a dense representation of the data for the experiment of the first experiment type, the dense representation being derived from the sparse representation by removing at least one empty data field from the sparse representation, and being presented in a relational database table defined according to the first set of one or more variable definition objects.

2. The method of claim 1, wherein the input specifying the first set of one or more variable definition objects includes input defining an experiment name, and, for each variable in the first set of one or more variable definition objects, input defining a variable name and a datatype.

3. The method of claim 1, wherein:
  the sparse representation includes an entry for each of the plurality of values; and
  the dense representation includes an entry representing values for two or more variables defined in the first set of variables.

4. The method of claim 3, wherein:
  each entry is a row in the corresponding relational database table.

5. The method of claim 3, wherein:
  the data for the experiment of the first experiment type includes values for a plurality of members of a library of materials; and
  the dense representation includes an entry representing values for two or more variables for a member of the library.

6. The method of claim 3, wherein:
  the dense representation includes columns corresponding to the defined variables.

7. The method of claim 1, further comprising:
  receiving a set of data for a second experiment type, the set of data including one or more values corresponding to a set of variables defined in a second pre-defined experiment class of the object model; and
  storing and presenting a representation of the data of the second experiment type in a relational database table defined according to the second pre-defined experiment class of the object model.

8. The method of claim 1, further comprising:
  receiving input specifying a second set of one or more variable definition objects defining a set of variables for a second experiment type, the variables in the set of variables for the second experiment type having types selected from the predefined set of data types;
  receiving data for an experiment of the second experiment type, the data including a plurality of values corresponding to variables defined in the second set of one or more variable definition objects;
  storing a sparse representation of the data for the experiment of the second experiment type in a relational database table according to the set of types defined by the second set of one or more variable definition objects; and
  presenting a dense representation of the data for the experiment of the second experiment type, the dense representation being derived from the sparse representation by removing at least one empty data field from the sparse representation, and being presented in a relational database table defined according to the second set of one or more variable definition objects.

9. The method of claim 1, wherein the relational database table for the dense representation of the data for the experiment of the first experiment type is presented in a name-value format.

10. A computer program product, tangibly stored on a non-transitory computer-readable medium, for processing experimental data in a laboratory data management system according to an object model, the object model including a first pre-defined experiment class that is configured to be instantiated to define one or more experiment objects that represent data for particular experiments in the laboratory data management system, the product comprising instructions operable to cause a programmable processor to:
- receiving, by a processor, input specifying a first set of one or more variable definition objects defining a set of variables for a first experiment type to be represented by one or more instances of the first pre-defined experiment class, the variables in the set of variables having types selected from a predefined set of data types including attributes that are configured to be used to represent data for experiments in the laboratory data management system;
- receiving, by the processor, data for an experiment of the first experiment type, the data including a plurality of values corresponding to variables defined in the first set of one or more variable definition objects;
- storing a sparse representation of the data for the experiment of the first experiment type in a relational database table according to the set of types defined by the first set of one or more variable definition objects; and
- presenting a dense representation of the data for the experiment of the first experiment type, the dense representation being derived from the sparse representation by removing at least one empty data field from the sparse representation, and being presented in a relational database table defined according to the first set of one or more variable definition objects.

11. The computer program product of claim 10, wherein the input specifying the first set of one or more variable definition objects includes input defining an experiment name and, for each variable in the first set of one or more variable definition, input defining a variable name and a datatype.

12. The computer program product of claim 10, wherein:
the sparse representation includes an entry for each of the plurality of values; and
the dense representation includes an entry representing values for two or more variables defined in the first set of variables.

13. The computer program product of claim 12, wherein:
each entry is a row in the corresponding relational database table.

14. The computer program product of claim 12, wherein:
the data for the experiment of the first experiment type includes values for a plurality of members of a library of materials; and
the dense representation includes an entry representing values for two or more variables for a member of the library.

15. The computer program product of claim 12, wherein:
the dense representation includes columns corresponding to the defined variables.

16. The computer program product of claim 10, further comprising instructions operable to cause a programmable processor to:
receive a set of data for a second experiment type, the set of data including one or more values corresponding to a set of variables defined in a second pre-defined experiment class of the object model; and
store and present a representation of the data of the second experiment type in a relational database table defined according to the second pre-defined experiment class of the object model.

17. The computer program product of claim 10, further comprising instructions operable to cause a programmable processor to:
receive input specifying a second set of one or more variable definition objects defining a set of variables for a second experiment type, the variables in the set of variables for the second experiment type having types selected from the predefined set of data types;
receive data for an experiment of the second experiment type, the data including a plurality of values corresponding to variables defined in the second set of one or more variable definition objects;
store a sparse representation of the data for the experiment of the second experiment type in a relational database table according to the set of types defined by the second set of one or more variable definition objects; and
present a dense representation of the data for the experiment of the second experiment type, the dense representation being derived from the sparse representation by removing at least one empty data field from the sparse representation, and being presented in a relational database table defined according to the second set of one or more variable definition objects.

* * * * *